United States Patent [19]

Kelman

[11] 4,343,050

[45] Aug. 10, 1982

[54] INTRAOCULAR LENSES

[76] Inventor: Charles D. Kelman, 150 E. 58th St., New York, N.Y. 10022

[21] Appl. No.: 167,923

[22] Filed: Jul. 14, 1980

[51] Int. Cl.³ ............................ A61F 1/16; A61F 1/24
[52] U.S. Cl. .......................................................... 3/13
[58] Field of Search .......................................... 3/13, 1

[56] References Cited

U.S. PATENT DOCUMENTS

| 4,092,743 | 6/1978 | Kelman | 3/13 |
| 4,118,808 | 10/1978 | Poler | 3/13 |
| 4,159,546 | 7/1979 | Shearing | 3/13 |
| 4,242,760 | 1/1981 | Rainin | 3/13 |
| 4,249,271 | 2/1981 | Poler | 3/13 |
| 4,251,887 | 2/1981 | Anis | 3/13 |

Primary Examiner—Ronald L. Frinks
Attorney, Agent, or Firm—Henry Sternberg

[57] ABSTRACT

A new intraocular lens, suitable for use in artificial lens implantations and having a light-focusing lens body and two position fixation means therefor, is disclosed. One position fixation means extends generally radially from a first region of the periphery of the lens body and the other position fixation means comprising a pair of support members extends generally radially from a second region of the periphery of the lens body spaced from the first region. At least one of the support members of said latter position fixation means is resiliently deformable between a normal undeformed condition, in which the entire lens will not pass through an incision in the eye of a given length and a deformed condition, in which the entire lens will pass through such given incision. During insertion of the lens into the eye, sufficient force is applied to the deformable position fixation means to maintain it in the deformed condition thereof. Following insertion, removal of the applied force results in the deformable position fixation means tending to spontaneously return to the normal condition thereof.

23 Claims, 8 Drawing Figures

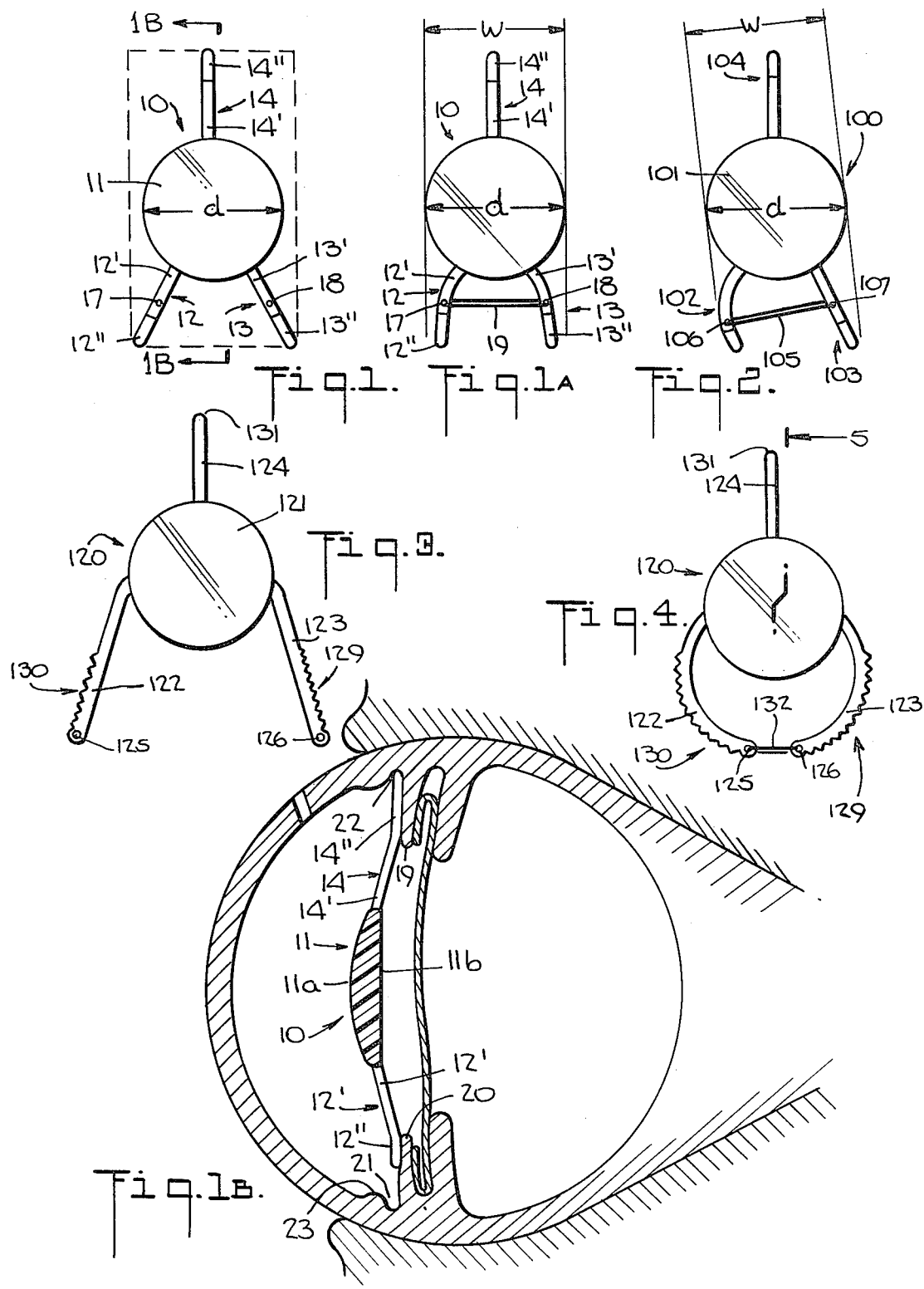

INTRAOCULAR LENSES

This invention relates to intraocular lenses suitable for use as artificial lens implants.

Intraocular lenses generally consist of a medial lens body and a plurality of lateral lobes or position fixation elements usually projecting from different sides of the lens body for use in fixing the lens in position in the eye.

As is well-known to those skilled in this art, even though the diameter of the lens body of an intraocular lens is only about 4 mm, a corneo-scleral incision considerably longer than the lens body diameter, and normally from about 8 to 9 mm in length, is normally required for lens implantation. An incision of this magnitude is mandated because the incision must be capable of being spread far enough to accommodate both the thickness and the width of the lens, i.e., the lens body and the position fixation elements extending therefrom. In this context, "thickness" means the dimension of the lens as measured from the anteriormost plane in which any part of the lens structure (e.g., the apex of the lens body) is found, to the posterior-most plane (e.g., the plane of the position fixation elements). "Width" means the minimum length of a projection of the lens onto a plane parallel to the optical axis of the lens body, in a direction perpendicular to a projection of the optical axis on such plane, which can be achieved by rotating the lens 360° about said optical axis.

Lens implantations are not only extremely difficult and delicate operations, but the use of certain currently available intraocular lenses, even by a highly skilled surgeon, entails a number of disadvantages. One of these is that a relatively long incision, generally double the diameter of the lens body or more, is required because of the mechanical, i.e., lens dimension, aspects mentioned earlier. The problem which ensues here is, of course, that the longer the incision, the greater the wound and the more difficult the post-operative recovery and healing period for the patient. Another disadvantage is that many of the currently available lenses are somewhat difficult to manipulate, given the relatively cramped environment of the surgical operation involved. An improper fixation of the lens relative to the pupil thus can easily occur, which would make it necessary for the surgeon, despite the possible traumatic effects on the patient, to go back into the eye after the initial surgery in order to correct the positioning error.

In my U.S. Pat. No. 4,092,743, issued June 6, 1978, a new intraocular lens construction, suitable for use in artificial lens implantations and having a medial light-focusing lens body and two lateral position fixation elements therefor, is disclosed. By virtue of the special shape of the position fixation elements, the lens can be introduced into the eye by being in effect "snaked through" the corneo-scleral incision. The length of the incision thus can be considerably less than is required in cases of lens implantations utilizing previously available intraocular lenses and still provide a three-point support for the lens in the eye so as to maintain proper lens positioning relative to the pupil of the eye.

It is an important object of the present invention to provide an alternate class of novel intraocular lenses which will also both substantially simplify lens implantation surgery and enable the disadvantages of the prior art lenses to be minimized if not avoided altogether.

A more particular object of the present invention is the provision of intraocular lenses so constructed that they will enable use of a corneo-scleral incision of considerably less length than had been required prior to those of my above-described inventions in implanting lenses having supports spaced apart a distance which exceeds the diameter of the lens body.

Further objects of the present invention are the provision of an intraocular lens that may be deformed into a temporary smaller configuration prior to and during insertion and a final larger configuration once it is in the eye, and an intraocular lens having a combined peripheral extent greater than the lens body alone but insertable through an incision the size of which is the minimum length required for insertion of just the lens body alone.

Other objects and features will be in part apparent and in part pointed out hereinafter.

Basically speaking, the objectives of the present invention are achieved by an intraocular lens construction which is characterized by a medial lens body and two position fixation means joined to and projecting from spaced, generally opposite, lateral peripheral regions of the lens body, at least one of the position fixation means being deformable and including a first and a second support member, at least one of which is resiliently deformable toward and away from the other such support member in a circumferential direction with respect to the lens body. The other position fixation means includes a third support or stabilizing member joined to an opposite peripheral section of the lens body.

In one form of the invention the deformable position fixation means include means for temporarily deforming at least one of the first and second support members by an applied force, preferably with a suture. In such embodiment of the invention, the first and second support members are integrally joined to a generally circular lens body and, in the undeformed condition, extend substantially radially therefrom at a predetermined angle with respect to each other. When the members are in such undeformed state, the remote edge portions of these support members are spaced apart a distance that is greater than the diameter of the lens body. When one or both of the support members are temporarily deformed during insertion, the deformation is such that no portion of one of these members is spaced from a corresponding portion of the other of these members a distance in excess of the lens body diameter. The third support member is preferably formed as an integral part of the lens body and need not be deformable.

In another representative form of the invention, both the first and second support members are deformable and the third member functions primarily to stabilize the lens in the eye while virtually all of the lens support function is performed by the first and second support members. This form of the invention is further distinguished from the embodiment of the preceding paragraph in that the first and second support members need not be deformable to the extent necessary to permit passage of the lens through a minimum length incision. Rather the flexibility of the first and second support members is utilized to permit insertion of the lens in contracted form through an incision in the eye which, although not of "minimum length", is still of significantly less length than would be required in order to accomodate a prior art lens that would provide equivalent support to the lens body once the lens is implanted in the eye.

The lens body and associated position fixation means are inserted in the eye through a corneo-scleral incision with the first position fixation means in a deformed, i.e., contracted condition. The contracted condition is achieved by utilizing suitable means to exert sufficient force to temporarily bring the one or more resiliently deformable support members of the first position fixation means more closely together in a plane generally perpendicular to the optical axis of the lens body. After insertion into the eye, the intraocular lens is restored to substantially its original shape by removal of the force imposed on the resiliently deformable support member(s).

The configurations of the two position fixation means in the undeformed condition of the deformable support member(s) and their location with respect to the lens body are such that first, the minimum length of a projection of the entire lens onto a plane parallel to the optical axis of the lens body in a direction perpendicular to a projection of the optical axis on the plane which can be achieved by rotating the lens 360° about the optical axis, is greater than the minimum length of a projection of the lens body alone onto the plane in a direction perpendicular to a projection of the optical axis on the plane which can be achieved by rotating the lens body 360° about the optical axis; and second, the difference between these lengths is such that an insertion of the lens, through an incision in the eye, by a movement which is generally radial with respect to the optical axis would require the length of the incision to be greater than the minimum possible length of the incision which, as a function of the thickness and lateral dimensions of the lens body, would accommodate and permit passage of the lens body alone. However, when the lens is in the deformed, i.e. contracted, state, the maximum transverse dimension of each position fixation means at any part thereof is such that it can be accommodated in and pass longitudinally through an incision of significantly less length than would be required for the lens in uncontracted form.

In some embodiments of the invention the lens will pass through a minimum length incision when the lens is in the contracted state. As used herein, the expression "minimum length incision" means that minimum size incision required in the eye to permit passage of the lens body alone therethrough. The size of the minimum length incision will vary as a function of the lens body dimensions in two directions i.e., (1) along the optical axis and (2) perpendicular to the optical axis.

In an intraocular lens according to one embodiment of the present invention, which is particularly suited for an implantation in which the first and second position fixation means are to be seated behind the iris in the lower and upper regions, respectively, of the cul-de-sac formed by the anterior and posterior capsules, the two position fixation means are in substantially coplanar relation with one another.

In use, when a lens according to the present invention that will pass through a minimum length incision is being implanted, the surgeon will first make a corneoscleral incision in the eye only slightly longer than the diameter of the lens body, i.e., the incision will be about 5 mm in length. In order to insert the lens into the eye, the surgeon will ensure that the first position fixation means is in contracted form, e.g., via a suture, and then introduce the lens generally longitudinally into the eye. When the lens is to be implanted in the anterior chamber, the force holding the first position fixation means in a contracted state is removed after insertion and after the lens has assumed its normal configuration it may then be properly positioned and implanted in the anterior chamber. On the other hand, when a lens according to the invention is to be implanted in the posterior chamber, it is preferred to allow the lens to assume an uncontracted configuration only after the latter is located in the posterior chamber and properly oriented so that the expanding deformable fixation means will automatically enter the cul-de-sac formed by the anterior and posterior capsules upon removal of the contracting force. It will be understood that in both cases the two position fixation means, upon release of the resiliently deformable first position fixation means, will cooperate to maintain the proper disposition of the lens body relative to the pupil of the eye.

When a lens of the invention that will not pass through a minimum length incision is being implanted, the length of the incision will of course have to be adjusted to the minimum dimension attainable by contraction of the deformable position fixation means.

The foregoing and other objects, characteristics and advantages of the present invention will be more clearly understood from the following detailed description thereof when read in conjunction with the accompanying drawings, in which:

FIG. 1 is a plan view of an intraocular lens according to one embodiment of the present invention;

FIG. 1A is a plan view of the intraocular lens of FIG. 1 in contracted condition ready for insertion into the eye;

FIG. 1B is a sectional view of the intraocular lens of FIG. 1 after implantation, taken along the line 1B—1B in FIG. 1 and also including a diagrammatic, substantially vertical section through a human eye;

FIG. 2 is a plan view of an intraocular lens according to another embodiment of the invention, in which the lens is in a contracted condition preparatory to insertion;

FIG. 3 is a plan view of a preferred form of intraocular lens according to the present invention in normal, i.e., uncontracted, condition e.g. prior to insertion;

FIG. 4 is a plan view of a FIG. 3 lens in contracted condition preparatory to insertion.

Figure 5:
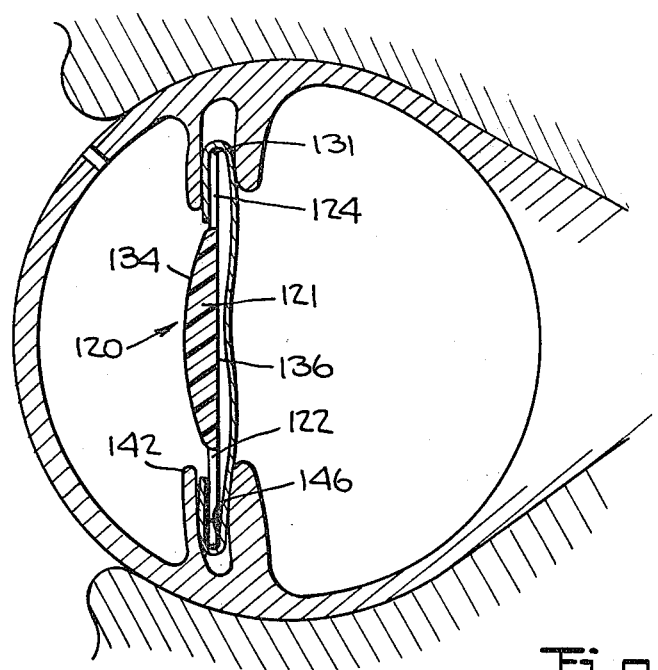
FIGS. 5 and 6 are diagrammatic views respectively showing a FIG. 3-type lens in position in a vertical cross-section of the eye and in a frontal view of the eye with the lens being prevented from expanding to its uncontracted condition by the interior of the eye.

Referring now to the drawings in greater detail, an intraocular lens 10 according to one embodiment of the present invention is shown in FIGS. 1, 1A and 1B. The lens 10 consists of a lightfocusing lens body 11 having a convex anterior surface 11a and a flat posterior surface 11b, first position fixation means comprising support members 12 and 13 and second position fixation means comprising support member 14. The intraocular lens 10 of this embodiment is designed for implantation anteriorly of the iris 20.

The support member 12, which extends generally laterally from one region of the periphery of the lens body 11, comprises portions 12' and 12" which are not coplanar with each other or with the lens body. The first portion 12' is inclined somewhat posteriorly of the lens body from the region of its connection to the same, and the second portion 12" is disposed entirely posteriorly of the lens body and in a plane generally parallel to the plane of the lens body. Support member 13 is substantially identical to support member 12 with the angle between support members 12 and 13 being approximately 60°. Support member 14 extends generally laterally from a second region of the periphery of the lens body spaced from and generally opposite the region where first position fixation means comprising support members 12 and 13 are located. As with the other support members, the support member 14 has a first inner portion 14' which is inclined somewhat posteriorly of the lens body 11 from the region of its connection to the same, and a second outer portion 14" which is disposed entirely posteriorly of the lens body and in a plane generally parallel to the plane of the lens body.

Although by virtue of the foregoing arrangement the three support members 12, 13 and 14 of the first and second position fixation means are not coplanar with the lens body, the degree of inclination of the first portions 12', 13' and 14' of the support members is such as to dispose the second portions 12", 13" and 14" of the support members in coplanar relation with each other and with their posterior surfaces at a perpendicular distance of about 0.25 to 0.75 mm from the posterior surface 11b of lens body 11. By virtue of this arrangement, therfore, when the lens 10 has been implanted in a human eye, as shown in FIG. 1B, the lens body 11 and the proximate portions 12', 13' and 14' of the position fixation means will be maintained out of contact with the iris 20 in the region of the pupil, thereby minimizing the possiblity of the lens irritating the iris and interfering with the expansion and contraction of the pupil 19. Preferably, both position fixation means are unitary with the lens body, i.e., they are not separately attached but are formed with the lens body (by molding or machining, for example) of any suitable physiologically inert and non-toxic synthetic plastic material such as is well known to the art, e.g., polymethylmethacrylate, but the position fixation means may, as long as they have the requisite shapes, orientations and properties, comprise materials different than used for the lens body.

It will be noted from FIG. 1, which illustrates an anterior chamber lens, that the distance between the most remote edges, i.e., the free ends of portions 12" and 13" of support members 12 and 13 defines a first dimensional side 15 of a rectangle shown in dotted outline in FIG. 1. The distance from a line joining the free ends of portions 12" and 13" to the free end of portion 14" of support member 14 defines a second dimensional side 16 of the rectangle. The rectangle, which encloses the entire structure of the intraocular lens 10, does not contact any portion of the periphery of the lens body 11. In FIG. 1, intraocular lens 10 is shown in its manufactured shape or configuration, which also corresponds to the configuration of the lens after it is implanted. In FIG. 1A, the intraocular lens 10 is shown in the contracted condition i.e. the condition in which the lens is inserted into the eye preparatory to implantation. To permit temporary contraction of support members 12 and 13 during insertion of intraocular lens 10 into the eye, support members 12 and 13 are both deformable to such extent that a properly applied force will bring support members 12 and 13 closely enough together so that the maximum width dimension W between the most remote edges of said support members 12 and 13 will not exceed the diameter d of the lens body 11. As a result the intraocular lens 10 may be inserted through a corneo-scleral incision that is the minimum size necessary to accommodate lens body 11. Since it is desired that the lens shape after implantation correspond to the initial manufactured shape, the materials used in the construction of support members 12 and 13 are chosen such that the elastic limit of these support members should not be exceeded when they are brought into the contracted condition shown in FIG. 1A.

As shown in FIG. 1A, intraocular lens 10 is provided with means permitting application of the force necessary for contraction of the support members, namely the apertures 17 and 18, respectively. A suture 19, threaded through each of the apertures, is shown sufficiently tightened to draw support members 12 and 13 closely enough together that the width dimension w between the remote edges of these support members is nowhere greater than the diameter d of lens body 11. Of course, the force for contracting the support members need not be provided by a suture, but could instead be provided by other means, e.g., by a tool such as a miniature pliers which the surgeon could use to hold the support members in deformed condition during insertion.

In use, an incision is made about 5 mm long, i.e. just sufficient to enable it to spread to the degree required to accomodate both the diameter and the thickness of the lens body 11. With the incision properly spread apart, lens 10 in the contracted condition shown in FIG. 1A, i.e., with the support members 12 and 13 deflected toward one another, is then inserted essentially "longitudinally" into the eye through the incision, starting, for example, with the free end of support member 14. The lens body 11 and the first position fixation means comprising support members 12 and 13 are then fed through the incision.

Upon completion of the passage of the lens through the incision into the eye, the force which is used to retain the support members 17 and 18 in deformed condition is removed, whereupon lens 10 automatically assumes the shape desired for implantation, i.e., in this embodiment, the original manufactured shape shown in FIG. 1. The free ends of the two support members 12 and 13 are then guided into the lower regions 21 of the groove located behind the scleral spur 23 and the free end of the support member 14 into the upper region 22 of the same groove. In those cases where a suture 19 is used to provide the force for deforming, that force is removed by cutting of the suture after the lens is in the eye.

The ultimate position of the lens 10 is such that the entire lens is positoned anteriorly of the iris, with the second portions 12" and 13" of the first position fixation means and the second portion 14" of the second position fixation means seated in the lower and upper regions 21 and 22, respectively, of the groove behind the scleral spur 23. The free ends of portions 12", 13" and 14" provide a three-point support for the lens in the eye so as to maintain the lens body in proper optical position relative to the pupil of the eye. One or more of the support members may then be sutured in place so as to ensure that the lens will maintain its position. According to the present invention the three supporting ends are in undeformed final condition spaced apart further than they could be had they been confined to a distance dictated by the lens body diameter.

In lieu of the apetures as a means of permitting application of sufficient force to deform the support members 12 and 13 forming the first position fixation means, as utilized in the embodiment of FIGS. 1, 1A and 1B, the aforementioned support members may be provided with serrations or notches (see FIG. 4), around which a suture may be looped and tightened to the degree necessary to bring these support members into the previously described deformed, i.e., contracted, condition preparatory to insertion of the lens into the eye.

The intraocular lens 100 according to the FIG. 2 embodiment is identical in all respects with the lens 10 of FIGS. 1, 1A and 1B except that only one of the two support members comprising the first position fixation means is deformable toward the other of said support members. Thus lens body 101 and support members 102 and 104 are as described for lens body 11 and support members 12 and 14 respectively, of FIGS. 1, 1A and 1B. Support member 103 of FIG. 2 need not be deformable but is otherwise the same as support member 13 of FIGS. 1, 1A and 1B. The FIG. 2 embodiment is shown in a contracted position achieved via suture 105 being looped through apertures 106 and 107 and sufficiently tightened to reduce the maximum distance between the most remote edges of support members 102 and 103 to not more than the maximum dimension of lens body 101.

FIGS. 3 and 4 respectively show a preferred embodiment of a posterior chamber lens according to the present invention in undeformed and in contracted condition. Intraocular lens 120 comprises lens body 121 and the first position fixation means comprise a pair of resiliently deformable support members 122 and 123 and the second position fixation means comprise stabilizing member 124. The lens is intended for implantation in the posterior cavity. As shown in FIG. 4, when the lens is in contracted form the deformable support members 122 and 123 form a serrated pincer-like shape. As shown, each of the deformed or contracted support members 122 and 123 has a concave edge and a convex edge forming a generally "C"-shaped member. The concave edges of the support members face each other, resulting in the pincer-like shape. A series of serrations or notches 129 and 130 are provided on the convex edge of each of the members. In the illustrated embodiment, the serrations on each support member extend from the free end of the member to about the mid-point of the "C". Serrations or notches 129 and 130 serve to enhance the position-fixation ability of support members 122 and 123. Holes 125 and 126 located near the free ends of support members 122 and 123 provide a means of applying sufficient deformation force via a suture 132 as shown (or a pliers-like instrument) to the first position fixation means to bring the lens 120 from the uncontracted state shown in FIG. 3 to the contracted configuration of FIG. 4 for insertion.

Figure 6:
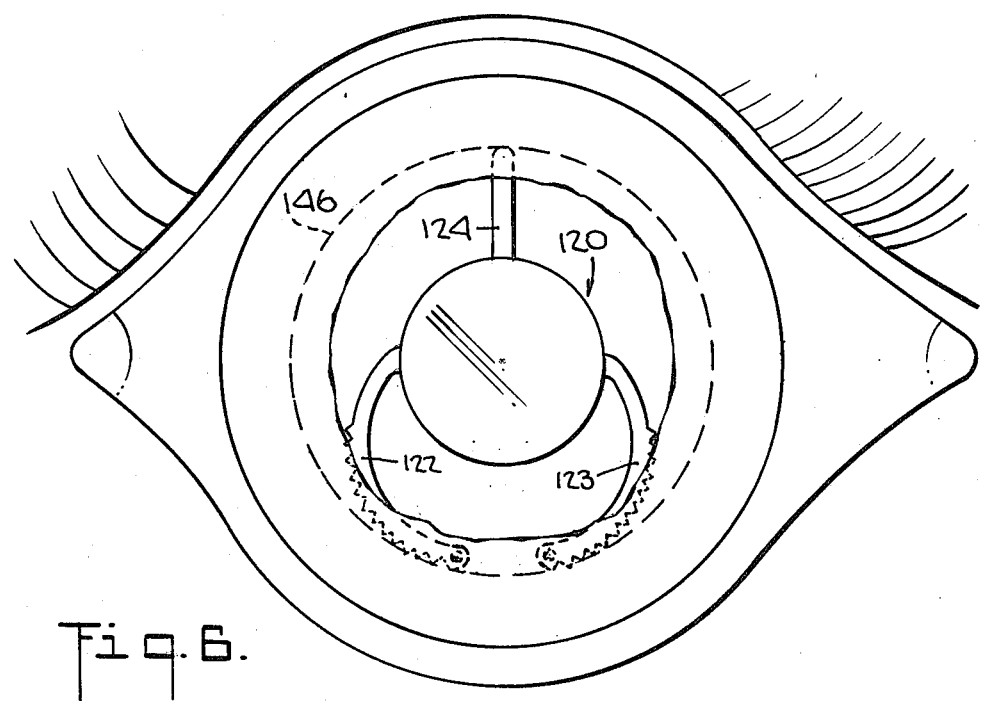

Intraocular lens 120 of the instant embodiment (FIGS. 3 and 4) comprises first and second position fixation means which are to be seated behind the iris in the lower and upper regions, respectively, of the cul-desac formed between the anterior and posterior capsules. As shown in FIG. 5, which is a diagrammatic view of a vertical cross-section through the eye illustrating the relative location of the implanted lens, the lens body 121 comprises a convex anterior surface 134 and a flat posterior surface 136. The posterior surfaces of all three support members comprising the first and second position fixation means are coplanar with each other and with posterior surface 136 of the lens body, as partially shown in FIG. 5. Thus, in this embodiment of the invention, the position fixation means are coplanar with the lens body. Although support members 122 and 123 of the first position fixation means are so designed and used that they tend to re-assume their original configuration following removal of suture 132, their lengths and shapes are preferably chosen such that there is not sufficient room in the cul-de-sac 146 for the original shape to be re-assumed. Consequently, the remote sides of the free ends of the support members are met by slight restraining forces arising from their contact with the afore-mentioned cul-de-sac, as shown in FIG. 6. Notches or serrations 129 and 130 result in the formation of multiple edges on the remote side of each support member comprising the first position fixation means, which edges, coupled with the above-mentioned slight restraining forces, increase the ability of those support members to fix the position of the lens in the eye. Stabilizing member 124 serves primarily to maintain the lens in the proper position with respect to the vertical plane of the lens body.

FIG. 6, a diagrammatic front view of a human eye, illustrates lens 120 in implanted position with deformable support members 122 and 123 under compression and therefore being gently urged against the inner peripheral surface of the cul-de-sac 146 formed between the anterior and posterior capsules. Thus, a lens embodying the features of the FIG. 4 embodiment may dispense with the need for suturing the lens in place since the serrated edges of the first position fixation means, being urged slightly outwardly into engagement with the inner surface of the cul-de-sac as a result of the members 122 and 123 being restrained by the cul-de-sac, prevent the lens from returning to the undeformed condition. The dimensions of the lens are preferably chosen such that in implanted condition the deformable support members are not fully sprung to their undeformed condition and are configurated and manufactured to exert only that slight degree of pressure against the cul-de-sac which is known by those skilled in the art to be safely accomodated by the eye.

The dimensions provided certain of the intraocular lenses according to this invention will vary according to eyeball measurements for each patient, although the embodiment illustrated in FIGS. 3 to 6 will adapt itself to various sizes of the eye within a limited range. Nevertheless, as illustrative only and in order to exemplify the magnitudes of the dimensions being dealt with, the overall length of an intraocular lens in final, non-contracted condition from the free ends of the first position fixation means to the free end(s) of the second position fixation means is approximately 12-13 mm; the diameter of the lens body is approximately 4 mm; the thickness of the lens body is approximately 0.4 mm; the angle between the portions of the first and second support members that are closest to the periphery of the lens body in embodiments according to FIGS. 1 and 2 is preferably, but not necessarily, approximately 60°, while in embodiments according to FIG. 3 such angle may approach 180°; the distance between the remote edges of first and second support members at points of contact with the eye is typically approximately 7 mm when there is only one contact point per support member; the cross-sectional width of typical support members is approximately 1.2 mm; the cross-sectional thickness of typical support members is approximately 0.2 mm; and the offset between the main portions and the seating portions of the support members for implantation anteriorly of the iris is approximately 0.7 mm.

It is apparent that many variants on the structures described herein are possible without departing from the nature of the invention, such as by slight modification of support members and varying the selection of same for use in a particular lens embodiment. Thus intraocular lenses according to the invention may be provided with both the first and second position fixation means being deformable, resulting in four widely spaced support points where, for example, both position fixation means are of the sort illustrated for the first position fixation means of FIG. 1. Moreover, it should also be apparent from this disclosure that lens embodiments described in the context of anterior chamber lenses may be configured for posterior chamber implantation by suitable modification of the support members from the FIG. 1B to the FIG. 5 configuration.

I claim:

1. An intraocular lens with flexible support suitable for use as an artificial lens in the interior of a human eye and insertable through an incision in said eye, said eye interior having groove portions extending circumferentially at lower and upper portions of the eye when viewed in cross-section, said lens comprising a light-focusing lens body with first and second peripheral sections, and first and second position fixation means respectively joined to said first and second peripheral sections of said lens body and extending generally radially beyond said peripheral sections, said position fixation means being respectively engageable with the corresponding one of said groove portions, at least one of said position fixation means being resiliently deformable, in response to a force applied thereto, between a first undeformed condition, and second deformed condition, said deformable position fixation means being capable of spontaneously returning toward substantially said first condition thereof upon removal of said applied force after said lens has been inserted into the eye, and wherein said deformable position fixation means comprises first and second support members extending generally outwardly of said lens body and each having a free end, said free ends being spaced apart a first distance when in said first undeformed condition, and spaced apart a second distance less than said first distance when in said second deformed condition, each of said first and second support members having at least one portion thereof defining a seating portion which contacts the adjacent groove portion of the eye, and wherein said second position fixation means comprises a stabilizing member, wherein said first and second support members of said deformable position fixation means are non-overlapping when viewed in the direction of the optical axis of said lens body in said first undeformed condition of said deformable position fixation means, and wherein said first and second support members of said deformable position fixation means are generally "C"-shaped when viewed in the direction of the optical axis of said lens body after said lens is implanted in the eye, the respective concave portions of the members face each other such that a line joining said free ends is not superposed within the periphery of said lens body.

2. An intraocular lens according to claim 1, wherein the dimensions of said deformable position fixation means are such as to preclude said deformable position fixation means from returning to substantially said first condition upon removal of said applied force after said lens has been inserted into the eye.

3. An intraocular lens according to claims 1 or 2, wherein in said first condition the distance between the circumferentially most remote edges of said deformable position fixation means precludes insertion of the lens through a minimum length incision and in said second condition the lens may be inserted into the eye through a minimum length incision.

4. An intraocular lens as in claim 1, wherein at least one of said first and second support members is resiliently deformable in a direction toward the other of said support members for reducing the distance between said circumferentially most remote edges of said deformable position fixation means.

5. An intraocular lens as in claim 1, wherein said second position fixation means comprises a third support member having a portion thereof defining at least one seating portion.

6. An intraocular lens as in claim 1, wherein said deformable position fixation means comprises means adapted to receive a force applied to said deformable position fixation means to deform said last-mentioned means.

7. An intraocular lens in claim 6, wherein said means for receiving said deformation force comprises at least one aperture.

8. An introacular lens as in claim 6, wherein said means for receiving said deformation force comprises at least one notch.

9. An intraocular lens as in claim 6, 7 or 8 further comprising a suture cooperating with said force receiving means to apply to said deformable position fixation means a deformation force.

10. An intraocular lens as in claims 6, 7 or 8 further comprising a suture cooperating with said force receiving means to apply to said deformable position fixation means a deformation force and wherein said deformation force applied by said suture is such that the distance between the most remote edges of said deformable position fixation means is no greater than would permit insertion of the lens through a minimum length incision.

11. An intraocular lens as in claim 1, wherein each said first and second support member is resiliently deformable toward the other of said support members in a direction generally circumferential with respect to the lens body.

12. An intraocular lens with flexible support suitable for use as an artificial lens in the interior of a human eye and insertable through an incision in said eye, said eye interior having groove portions extending circumferentially at lower and upper portions of the eye when viewed in cross-section, said lens comprising a light-focusing lens body with first and second peripheral sections, and first and second position fixation means respectively joined to said first and second peripheral sections of said lens body and extending generally radially beyond said peripheral sections, said position fixation means being respectively engageable with the corresponding one of said groove portions, at least one of said position fixation means being resiliently deformable, in response to a force applied thereto, between a first undeformed condition, in which the distance between the circumferentially most remote edges of said deformable position fixation means precludes insertion of the lens through an incision of a given length, and a second deformed condition, in which the distance between the circumferentially most remote edges of said deformable position fixation means is such as to permit insertion of the lens through said incision of given length, said deformable position fixation means being capable of spontaneously returning toward substantially said first condition thereof upon removal of said applied force after said lens has been inserted into the eye, and wherein said deformable position fixation means comprises first and second support members extending generally radially outwardly of said lens body, said first and second support members each having at least one portion thereof defining a seating portion which contacts the adjacent groove portion of the eye, and wherein said second position fixation means comprises a stabilizing member, and wherein said first and second support members of said deformable position fixation means in said second condition are generally "C" shaped, the respective concave portions of the members face each other and the convex portion of each of the members comprises a plurality of notches.

13. An intraocular lens suitable for use as an artificial lens in the interior of a human eye and insertable through an incision in said eye, said eye interior having groove portions extending circumferentially at lower and upper portions of the eye when viewed in cross-section, said lens comprising a light-focusing lens body with first and second peripheral sections, and first and second position fixation means respectively joined to said first and second peripheral sections of said lens body and extending generally radially beyond said peripheral sections, said position fixation means being respectively engageable with the corresponding one of said groove portions, one of said position fixation means being resiliently deformable, in response to a force applied thereto, between a first undeformed condition, and a second deformed condition, said deformable position fixation means being capable of spontaneously returning toward substantially said first condition thereof upon removal of said applied force and comprising first and second support members extending generally outwardly of said lens body, each of said first and second support members being resiliently deformable and each having a free end, said free ends being spaced apart a first distance when in said first undeformed condition, and spaced apart a second distance less than said first distance when in said second deformed condition, said first and second support members being non-overlapping when viewed in the direction of the optical axis of said lens body in said first undeformed condition of said deformable position fixation means, each of said first and second support members being generally "C"-shaped when viewed in the direction of the optical axis of said lens body after said lens is implanted in the eye, the concave portion of each of said last-mentioned members facing each other, such that a line joining said free ends is not superposed within the periphery of said lens body, the convex portion of each of said last-mentioned members comprising a seating portion for contacting the adjacent groove portion of the eye, the other position fixation means comprising a stabilizing member, said first, second and stabilizing members being engageable with said groove portions of the eye so as to align the lens body with respect to the pupil of the eye.

14. An intraocular lens with flexible support suitable for use as an artificial lens in the interior of a human eye and insertable through an incision in said eye, said eye interior having groove portions extending circumferentially at lower and upper portions of the eye when viewed in cross-section, said lens comprising a light-focusing lens body with first and second peripheral sections, and first and second position fixation means respectively joined to said first and second peripheral sections of said lens body and extending generally radially beyond said peripheral sections, said position fixation means being respectively engageable with the corresponding one of said groove portions, one of said position fixation means comprising first and second support members each having a free end, one of said first and second support members being resiliently deformable in response to a predetermined force applied thereto in a direction toward the other of said support members for reducing the distance between said free ends a predetermined amount, said deformable support member being capable of spontaneously returning toward substantially its undeformed condition upon removal of said applied force after said lens has been inserted into the eye, said lens further including a force applicator means connected to said first and second support members to establish said predetermined force on said one of said support members, the other of said support members being substantially nondeformable in response to said predetermined force.

15. An intraocular lens according to claim 14 wherein the dimensions of said first and second support members are such as to preclude said one of said support members from returning to substantially the nondeformed condition upon removal of the predetermined force after said lens has been inserted into the eye.

16. An intraocular lens according to claims 14 or 15 wherein the normal distance between the circumferentially most remote edges of said first and second support members precludes insertion of the lens through a minimum length incision and the reduced distance between said circumferentially most remote edges permits insertion of the lens into the eye through said said minimum length incision.

17. An intraocular lens according to claim 14 wherein said first and second support members extend generally radially outwardly of said lens body and each has at least one portion thereof defining a seating portion which contacts the adjacent groove portion of the eye.

18. An intraocular lens as in claim 14 wherein said second position fixation means comprises a stabilizing member.

19. An intraocular lens as in claim 14 wherein said second position fixation means comprises a third support member having a portion thereof defining at least one seating portion.

20. An intraocular lens as in claim 19 wherein said first and second support members and said second position fixation member each comprise a first portion and a second portion, each said second portion of a support member comprising said seating portions and each second portion being offset slightly posteriorly relative to said lens body and in a plane relative to the plane of said lens body, and each said first portion respectively connecting each said second portion and said lens body.

21. An intraocular lens as in claim 14 wherein said first and second support members each include at least one aperture.

22. An intraocular lens as in claim 14 wherein said first and second support members each include at least one notch.

23. An intraocular lens as in claim 14 wherein said force applicator means comprise a suture.

* * * * *